(12) United States Patent
Ahn et al.

(10) Patent No.: US 11,534,527 B2
(45) Date of Patent: Dec. 27, 2022

(54) METHOD FOR SUPPLYING INKS FOR THREE-DIMENSIONAL PRINTING, AND THREE-DIMENSIONAL PRINTING METHOD USING SAME

(71) Applicant: T & R BIOFAB CO., LTD., Siheung-si (KR)

(72) Inventors: Geunseon Ahn, Siheung-si (KR); Songwan Jin, Siheung-si (KR); Jinhyung Shim, Siheung-si (KR); Wonsoo Yun, Siheung-si (KR); Donggu Kang, Siheung-si (KR)

(73) Assignee: T & R BIOFAB CO., LTD., Siheung-si (KR)

( * ) Notice: Subject to any disclaimer, the term of this patent is extended or adjusted under 35 U.S.C. 154(b) by 736 days.

(21) Appl. No.: 16/097,863

(22) PCT Filed: May 2, 2017

(86) PCT No.: PCT/KR2017/004687
§ 371 (c)(1),
(2) Date: Oct. 31, 2018

(87) PCT Pub. No.: WO2017/192004
PCT Pub. Date: Nov. 9, 2017

(65) Prior Publication Data
US 2019/0142995 A1    May 16, 2019

(30) Foreign Application Priority Data

May 3, 2016    (KR) .................. 10-2016-0054397
May 2, 2017    (KR) .................. 10-2017-0056273

(51) Int. Cl.
*B29C 64/106*    (2017.01)
*B33Y 10/00*    (2015.01)
(Continued)

(52) U.S. Cl.
CPC ............ *A61L 27/20* (2013.01); *A61L 27/16* (2013.01); *A61L 27/18* (2013.01); *A61L 27/222* (2013.01);
(Continued)

(58) Field of Classification Search
CPC ......... B33Y 10/00; B33Y 30/00; B33Y 70/00; B29C 64/118; B29C 64/209;
(Continued)

(56) References Cited

U.S. PATENT DOCUMENTS

2004/0253365 A1* 12/2004 Warren .................. B33Y 30/00
427/2.1
2009/0324671 A1    12/2009 Ngo et al.
(Continued)

FOREIGN PATENT DOCUMENTS

CN    204839829    12/2015
EP    3438241    2/2019
(Continued)

OTHER PUBLICATIONS

EPO, Search Report of EP 17792906.4 dated Nov. 5, 2019.

*Primary Examiner* — Joseph S Del Sole
*Assistant Examiner* — John Robitaille
(74) *Attorney, Agent, or Firm* — Lex IP Meister, PLLC

(57) ABSTRACT

The present invention relates to a method of filling different two-kinds of multiple inks into an ink extruding member for a three-dimensional print and a method of three-dimensional printing using the filled ink, and relates to a three-dimensional printing method using multiple inks comprising a step of applying pressure to the retained multiple inks and extruding it into a single extruding port of the extruding part to prepare an ink extruded product and printing the ink extruded product.

18 Claims, 8 Drawing Sheets

(51) Int. Cl.
| | |
|---|---|
| *A61L 27/20* | (2006.01) |
| *A61L 27/24* | (2006.01) |
| *A61L 27/38* | (2006.01) |
| *B33Y 30/00* | (2015.01) |
| *B33Y 70/00* | (2020.01) |
| *B29C 64/209* | (2017.01) |
| *A61L 27/18* | (2006.01) |
| *A61L 27/54* | (2006.01) |
| *A61L 27/52* | (2006.01) |
| *A61L 27/16* | (2006.01) |
| *B29C 64/118* | (2017.01) |
| *A61L 27/22* | (2006.01) |
| *A61L 27/36* | (2006.01) |
| *B29C 64/112* | (2017.01) |
| *B29C 67/00* | (2017.01) |

(52) U.S. Cl.
CPC ........... *A61L 27/24* (2013.01); *A61L 27/3633* (2013.01); *A61L 27/38* (2013.01); *A61L 27/52* (2013.01); *A61L 27/54* (2013.01); *B29C 64/106* (2017.08); *B29C 64/118* (2017.08); *B29C 64/209* (2017.08); *B33Y 10/00* (2014.12); *B33Y 30/00* (2014.12); *B33Y 70/00* (2014.12); *A61L 2300/414* (2013.01); *B29C 64/112* (2017.08); *B29C 67/00* (2013.01); *B29K 2995/0021* (2013.01)

(58) Field of Classification Search
CPC ........ B29C 64/106; A61L 27/20; A61L 27/16; A61L 27/18; A61L 27/222; A61L 27/24; A61L 27/3633; A61L 27/38; A61L 27/52; A61L 27/54
See application file for complete search history.

(56) References Cited

U.S. PATENT DOCUMENTS

| | | |
|---|---|---|
| 2012/0322154 A1 | 12/2012 | Park et al. |
| 2014/0027952 A1 | 1/2014 | Fan et al. |

FOREIGN PATENT DOCUMENTS

| | | |
|---|---|---|
| JP | 2000-280356 | 10/2000 |
| JP | 3669942 | 7/2005 |
| KR | 10-2015-0073083 | 6/2015 |
| KR | 10-2016-0014220 | 2/2016 |
| KR | 10-2016-0030939 | 3/2016 |
| KR | 10-2016-0036619 | 4/2016 |
| WO | 2014-149279 | 9/2014 |
| WO | 2015-017579 | 2/2015 |
| WO | 2015-066705 | 5/2015 |
| WO | 2015-077262 | 5/2015 |
| WO | 2016-025871 | 2/2016 |

* cited by examiner

[Fig. 1]
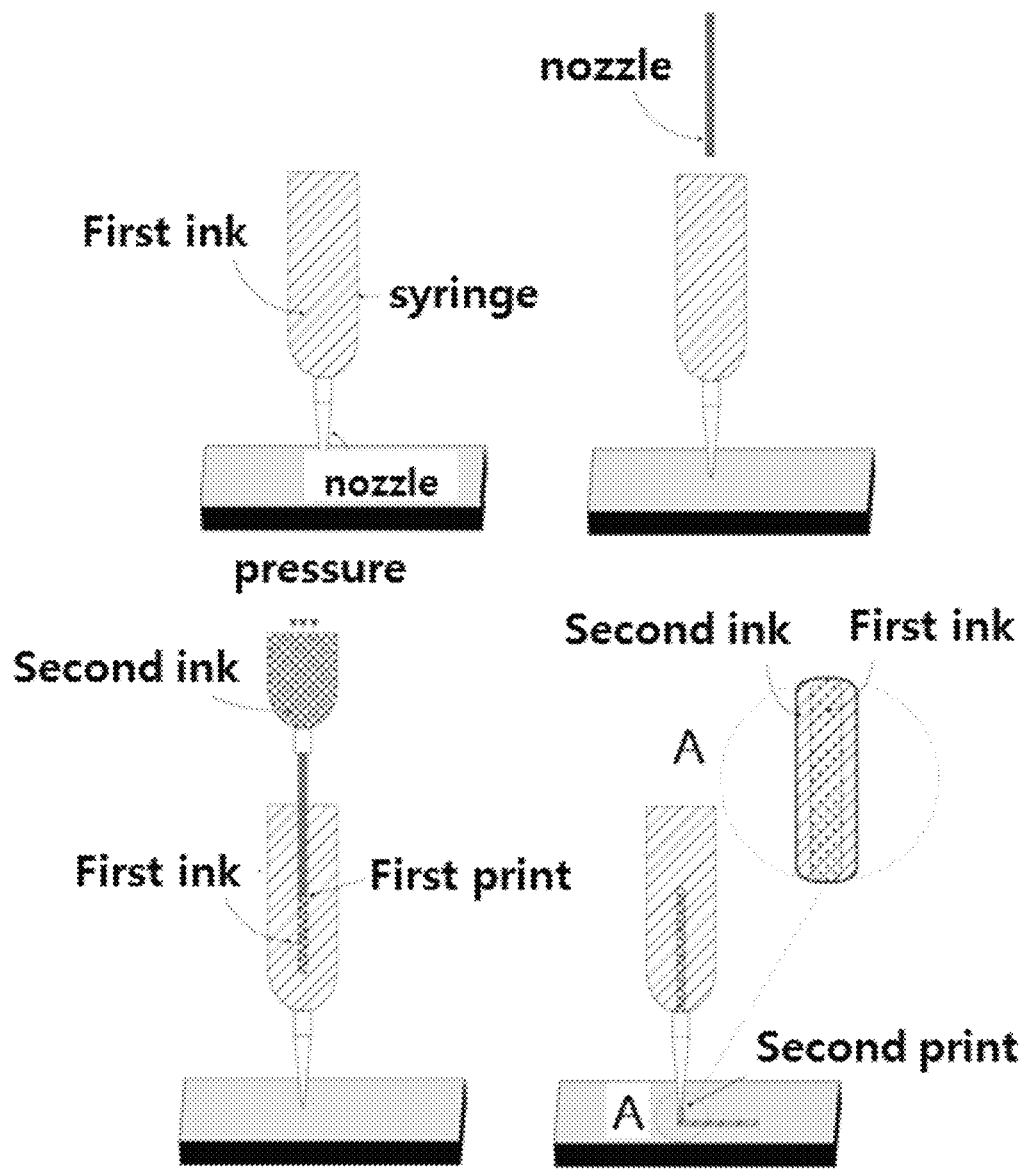

[Fig. 2]
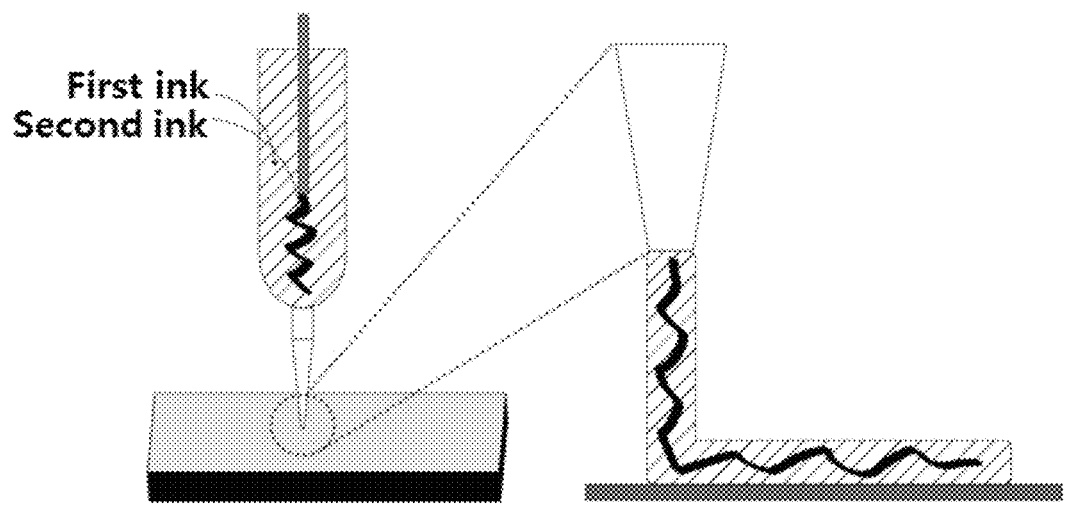
[Fig. 3]
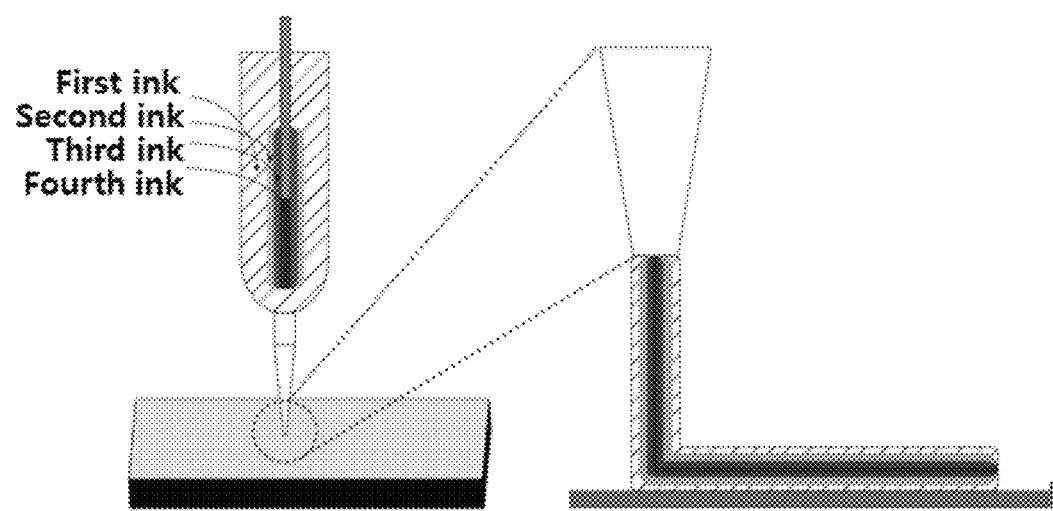

[Fig. 4]
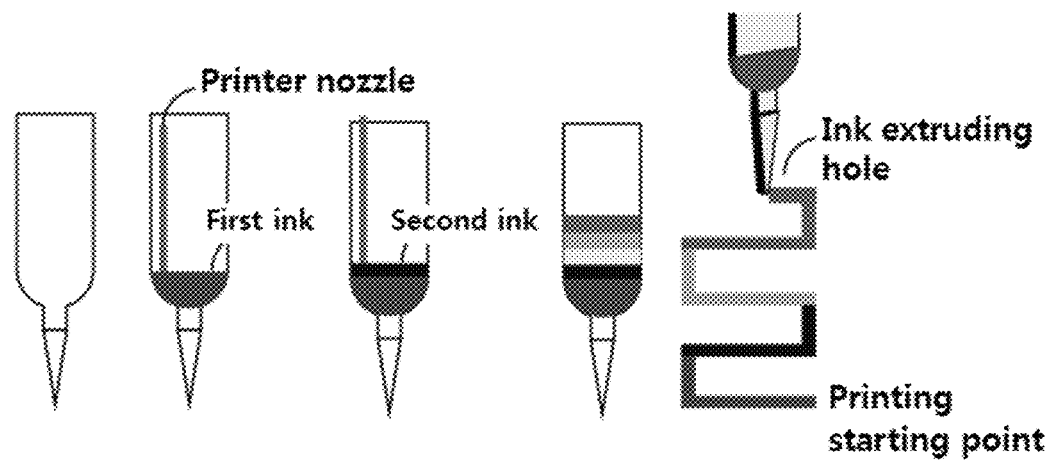
[Fig. 5]
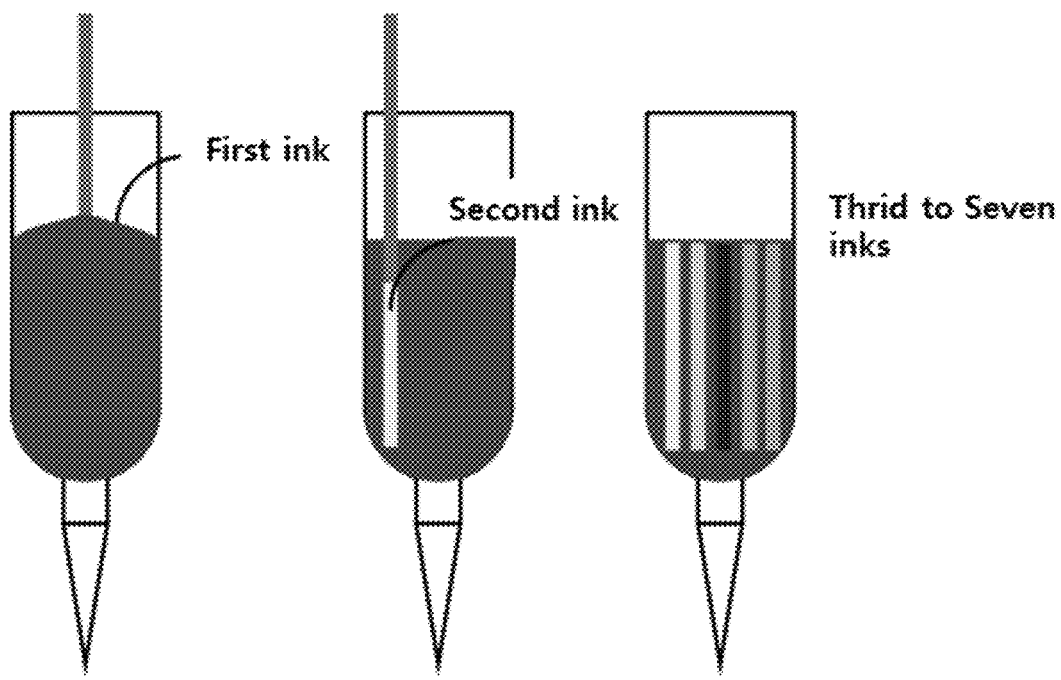

[Fig. 6]
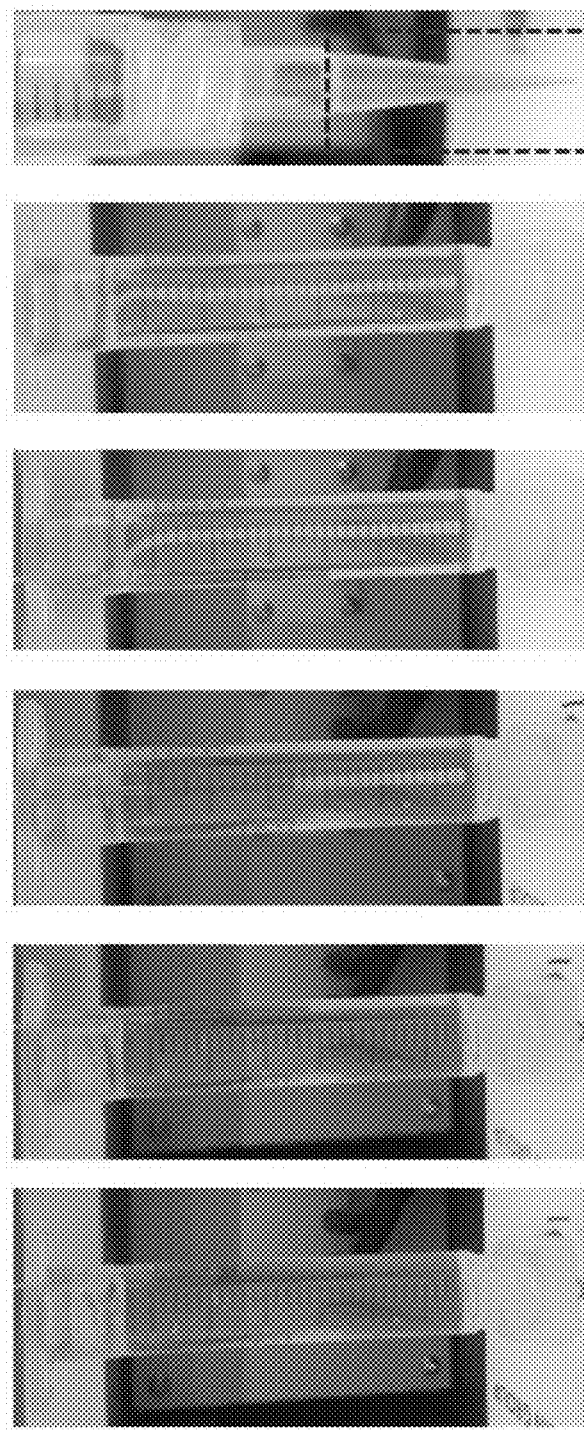

[Fig. 7]
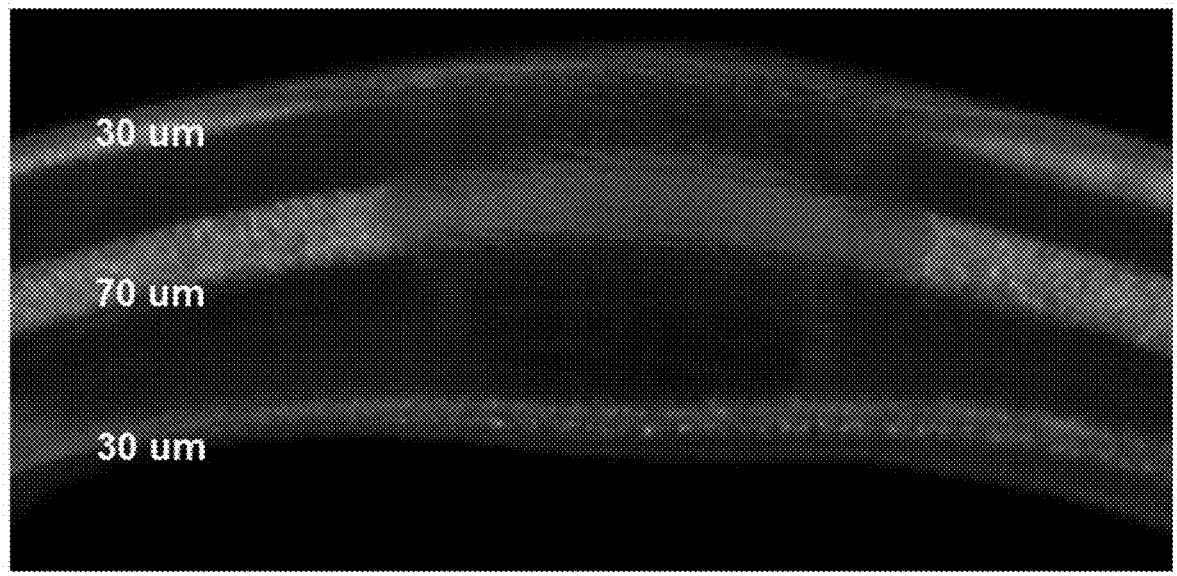

[Fig. 8]
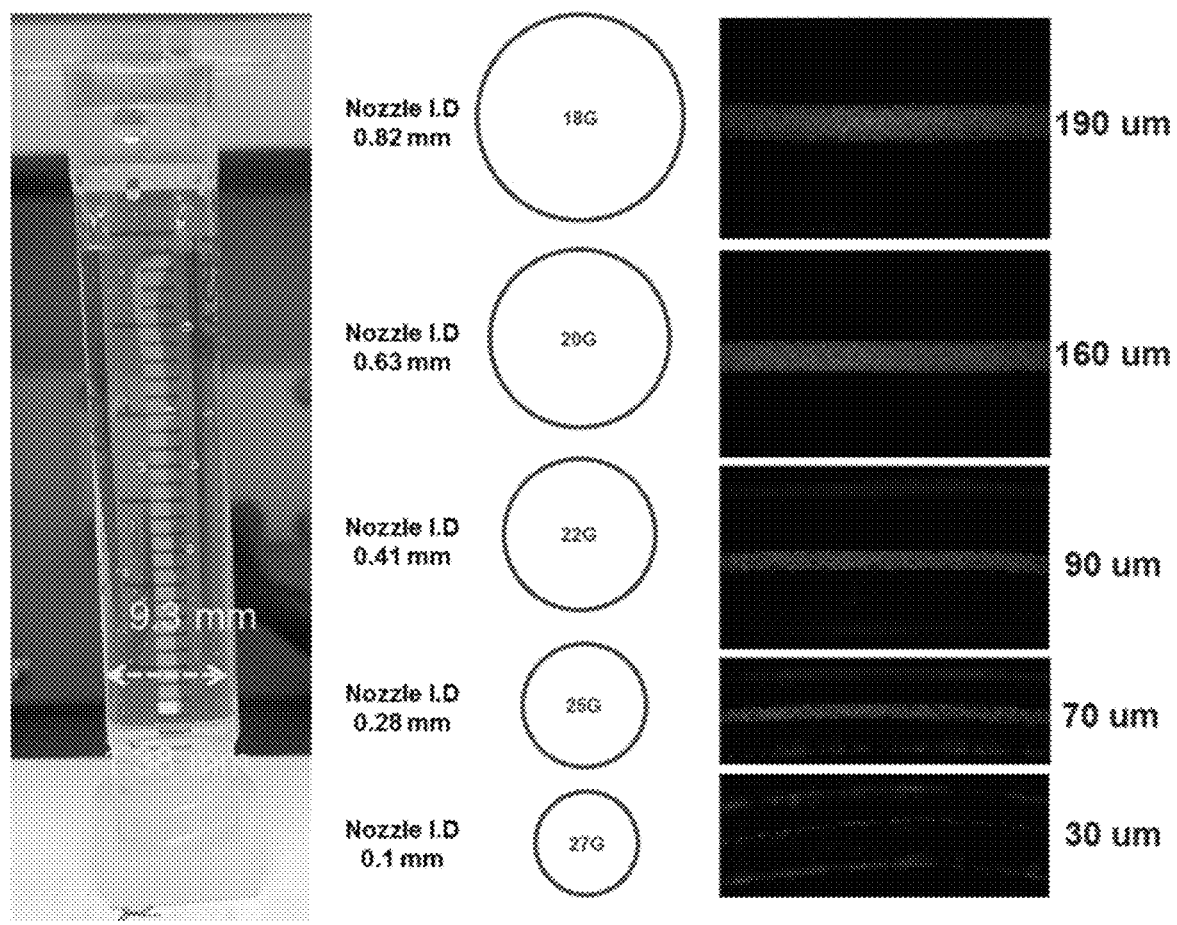

[Fig. 9]
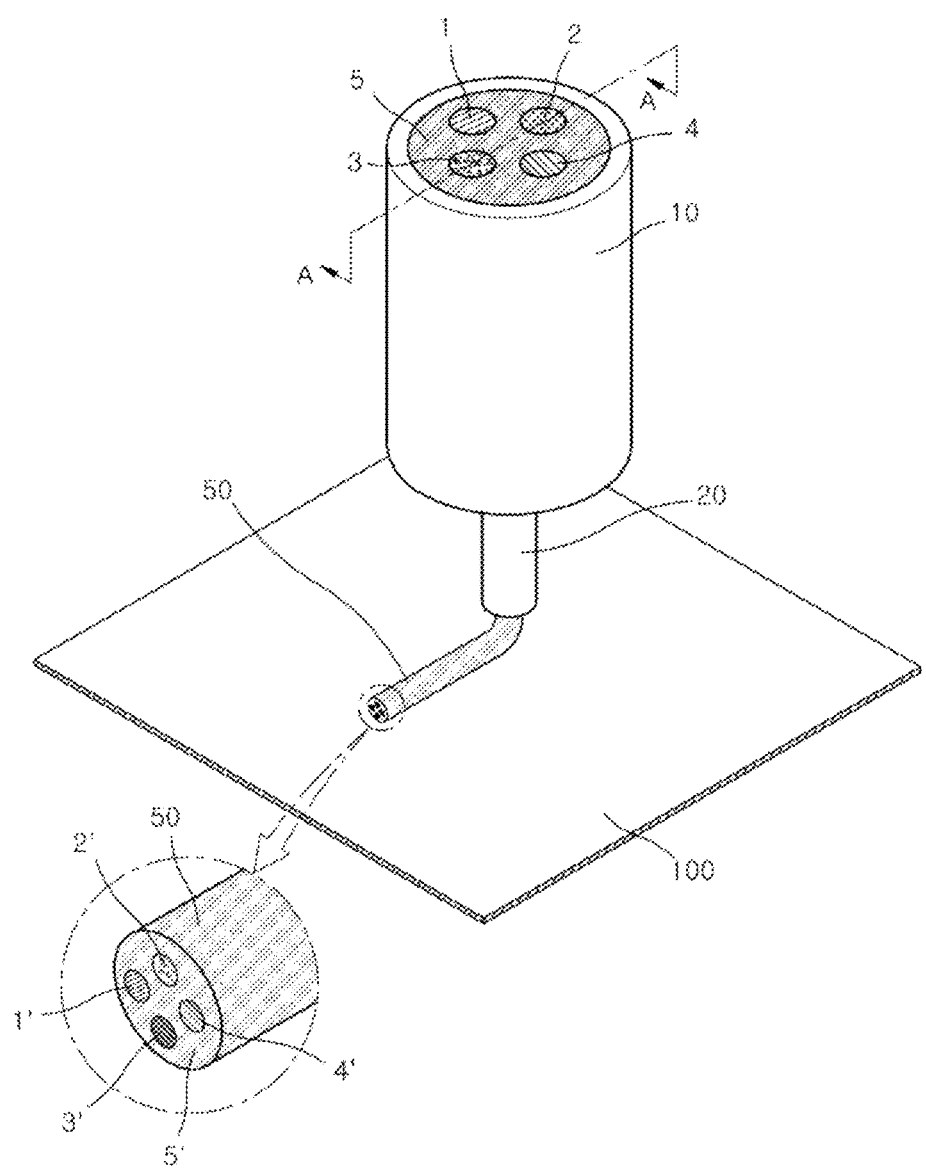

[Fig. 10]
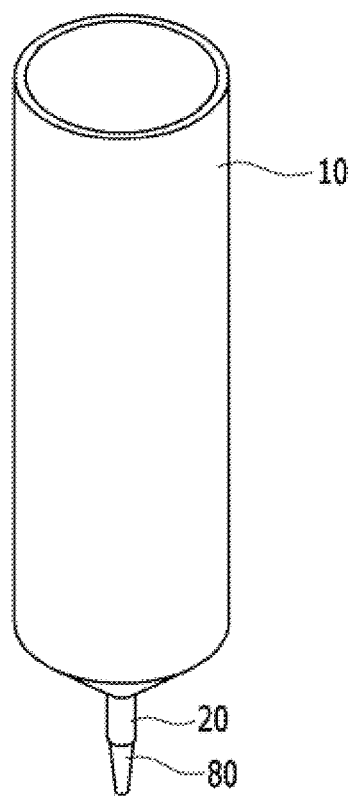

METHOD FOR SUPPLYING INKS FOR THREE-DIMENSIONAL PRINTING, AND THREE-DIMENSIONAL PRINTING METHOD USING SAME

TECHNICAL FIELD

The present invention relates to a method of providing inks to an ink receiving part of a three-dimensional printing device, a three-dimensional printing method comprising the method, and a three-dimensional printing device in which the method is applied, and more particularly, relates to a method of providing inks by a three-dimensional printing method into an ink receiving part equipped in a three-dimensional printing device, and a three-dimensional printing device in which the method is applied. The method of the present invention can make a biological tissue shape having a complicated structure with high precision.

BACKGROUND ART

Regenerative medicine and tissue engineering are mainly used to create a three-dimensional tissue structure as a field for restoring or replacing damaged organs, and bioprinting based on extrusion lamination shaping is one of the most suitable methods for creating such a three-dimensional tissue structure. Researches have been actively conducted to regenerate a functional tissue required through preparation of a cell structure similar to tissues constituting the human body using 3-dimensional (3D) bio-printing technology.

Head modules applied to the bio-printing technology are largely divided into an inkjet-based printing module and an extrusion-based printing module. In addition, various methods using laser, ultrasound, etc. have been proposed, but the two modules are most widely used.

Physical properties of a bio-ink required by such a bio-printing technology greatly vary depending on the printing head module. In the extrusion-based printing system, compared with the inkjet-based technology, there is no significant restriction on the viscosity of materials. Thus, in the extrusion-based printing system, the width of applicable biomaterials becomes much wider than the inkjet-based printing technology. In addition, since the extrusion-based printing system can easily make a thick layer to processed, a cell structure of a size required for clinical use can be easily prepared.

However, the resolution of the bio-printing technique based on the fused deposition modeling developed so far is several hundred micrometers, but the basic structure of organs or tissues in the human body is greatly different to a few tens of micrometers or less. In particular, the diameter of a capillary vessel supplying nutrients to a cell constituting organs or tissues is 3 to 4 micrometers, so it is difficult to implement it with current bio-printing techniques.

In addition, there is a case where multiple inks are used to print for bio-printing. For example, since the function of the cell is improved when dividing partitions between xenogeneic cells than simply mixing and spraying cells, in case of curing a hydrogel and a curing agent together or in case of co-culturing various kinds of cells, it is necessary to spraying multiple inks to bio-print. According to such a conventional method, it is attempted to solve it by using multiple heads containing multiple materials heterogeneously, but there is a disadvantage that the printing process time is increased and the cell viability is adversely affected and the system becomes complicated.

In order to increase the resolution of the printing technique, a nozzle having a small diameter should be used, but when the nozzle having a small diameter is used, there is a side effect of occurring shear stress between the material extruded from the inside of the nozzle and the wall during the extrusion, thereby reducing cell activity. Further, since there is a problem that cells are frequently killed by shear stress, it is difficult to blindly downsize the diameter of the nozzle.

DISCLOSURE

Technical Problem

The present invention relates to an ink extruding member which provides at least one of ink into an ink-receiving part by a three-dimensional printing method and prepares a printed product having a three-dimensional pattern using one extruded product, to prepare a biological tissue shape having a complicated structure using a three-dimensional printing method with high precision, and a printing method using thereof.

The present invention relates to a printing device preparing a printed product having a three-dimensional pattern using one extruded product comprising two or more of different inks and a printing method using thereof.

A purpose of the present invention is to provide a device of printing a biological tissue shape having a complex cross-sectional structure with high precision and resolution and a printing method using thereof.

The present invention provides a printing device and a printing method which can heterogeneously print a desired shape and simultaneously reduce shear stress of a cell significantly.

Technical Solution

The present invention relates to a three-dimensional printing method comprising an ink providing step of providing at least an ink as a printed ink product by a three dimensional printing method, into an ink-extruding member for three-dimensional printing comprising an ink receiving part and an ink extruding part, and preferably, the printing method may be applied to a bio-printing device and method used for fabrication of artificial tissues, organs, etc.

Another embodiment of the present invention comprises a step of providing at least an ink as a printed ink product by a three-dimensional printing method, into an ink-extruding member for three-dimensional printing comprising an ink receiving part and an ink extruding part, a step of applying physical force to the ink-extruding member, and extruding the received ink through the ink extruding part to form an extruded ink product, and a step of printing the extruded ink product on a plate.

The step of providing an ink, may provide at least one ink as an printed ink product made by a three-dimensional printing method, and when different 2 kinds or more of inks are used, at least an ink may be an filled ink product which is provided by a providing method other than the three-dimensional printing method. Specifically, at least two different inks can be provided as a filled ink product which fills at least a first ink into an ink receiving part and an ink printed product which prints at least one second ink by a three-dimensional printing method.

In the step of providing an ink, the printed ink product provided into the ink receiving member may have a two-dimensional or three-dimensional pattern itself, and a cross-section of the ink receiving member may also have the pattern. When the printed product is an artificial organ having one or more structures and various materials, the printing method of present invention is particularly useful or the artificial organ.

In addition, one embodiment of the present invention provides a three-dimensional printing method of a printed product having a cross-sectional pattern, where the ink extruding member may comprise a ink retained the ink receiving apart and an ink extruded product have the same shape of cross-sectional pattern as the three-dimensional printed product. It relates to a three-dimensional printing method of a printed product having a cross-sectional pattern, comprising a step of applying physical force to the ink retained in the space of the ink receiving part and extruding the ink through a nozzle connected to an extruding part, to prepare an extruded ink product having a cross-sectional pattern which is the same shape as the printed product; and a step of printing the extruded ink product on a plate.

In the three-dimensional printing method of the printed product having the cross-sectional pattern, the ink provided from the receiving part is printed to form one extruded ink product through an extruding part or a nozzle by being pressured, and the extruded ink product may have the same shape of cross-sectional pattern as the final printed product, and preferably, the ratio(=B/A) of the cross-sectional pattern of the extruded product or the final printed product(B) to the cross-sectional pattern of the ink retained in the ink receiving part, for example the ratio of the diameter or area of the cross-section may be downsized to a ratio of 100:99 to 100:0.1, 100:50 to 100:1, or 100:18 to 100:1. In addition, based on the ratio of diameter or area of the cross-section of the primary ink printed product provided by the three-dimensional printing method, the ratio of diameter or area of the cross-section of the secondary printed product to that of the primary ink printed product may be downsized to a ratio of 100:99 to 100:0.1, 100:50 to 100:1, or 100:18 to 100:1.

Other embodiment of the present invention relates to a three-dimensional printing device of a printed product having a cross-sectional pattern, comprising an ink extruding member comprising an ink receiving part retaining an ink for printing in the internal space, and an ink extruding part positioned in the lower part of the receiving part and equipped with a single passage which passes and extrudes the ink retained in the receiving part, a nozzle connected to the end of the extruding part, and a pressurizing member which applies physical force into the retained ink, where the ink is printed so as to have the same shape of the cross-sectional pattern as the printed product through the extruding part equipping the single passage.

The printing device according to the present invention may comprise means of applying physical force into the retained ink, and for example, it may apply pressure using a pressure device or screw, etc. The printing device of the present invention may apply a pressure using a single pressurizing member, or two or more of pressure members with the same pressure condition, so as to applying the same pressure into inks received in each of the partitioned space. The pressure is applied with the pressure member to each different ink, and the inks are printed through the ink extruding part equipped with a single passage, so as to have the same shape of cross-sectional pattern as the printed product. Thus, when using the printing device according to the present invention, there are advantages that a printed product having various cross-sectional patterns can be prepared, and in particular, a biological tissue having a complex cross-sectional structure can be prepared by printing with high precision and resolution with a three-dimensional method, and when comprising a cell in the biological tissue, a desired shape can be heterogeneously printed and the shear stress on the cell can be largely decreased.

Hereinafter, the present invention will be described in more detail.

The three-dimensional printing method according to the present invention comprises an ink providing step of providing at least one ink as an ink printed product printed by a three-dimensional printing method, into an ink extruding member for three-dimensional printing comprising an ink-receiving part and an extruding part, a step of preparing an ink extruded product by applying physical force to the ink extruding member and extruding the ink through an extruding part, and a step of printing the ink extruded product on a plate. According to the three-dimensional printing method according to the present invention, a printed product having a cross-sectional pattern may be prepared.

In the ink providing step, at least one ink may be further provided as an ink filled product by a method other than a three-dimensional printing method. In the present specification, the ink filled product means an ink filled product provided by a filling method, not the three-dimensional printing method, different from an ink printed product provided into an ink receiving member by a three-dimensional printing method, and as an example of the filling method by a method other than the three-dimensional printing method, there is a method of filling using a tube or syringe, etc., but not particularly limited.

The applying physical force may be conducted using a means to push an ink provided into an ink-receiving member to an extruding part, and for example, a pressure member or screw, etc. may be used. Specifically, the applying pressure may be performed by pressurizing using a single pressurizing member, or may be performed by pressurizing using two or more of pressurizing members. For example, the pressure may be applied as the same condition of pressure, and the same condition of pressure is a pressure condition that an ink is extruded to a single extruding port and a single ink extruded product can be formed, and preferably, means a pressure condition so that a single ink extruded product is formed by extruding two or more of different inks, or an ink printed product provided by a three-dimensional printing method and an ink filled product provided by a method other than a three-dimensional printing to a single extruding port, and the ink extruded product and a printed product prepared therefrom have the same shape as the cross-sectional pattern of the target printed product.

The three-dimensional printing method of a printed product with a cross-sectional pattern according to the present invention may be performed using the ink extruding member or the three-dimensional printing device comprising the ink extruding member according to the present invention.

The three-dimensional printing device of a printed product with a cross-sectional pattern according to other embodiment of the present invention may comprise an ink extruding member comprising a ink-receiving part that comprises a partitioning member providing two or more spaces partitioned so as to have the same shape of cross-sectional pattern as the printed product and receives each different ink in the spaces partitioned by the partitioning member, and an ink-extruding part which is positioned in the lower part of the ink-receiving part and is equipped with a single passage in which inks pass and extrudes inks received in the ink-receiving part, and in addition, may further comprise a nozzle linked to the ink-extruding part, and a pressure member applying pressure to inks received in each of the partitioned spaces.

In addition, the three-dimensional printing device may comprise a plate printing the extruded product and components comprised in common three-dimensional printing devices as an additional device for printing.

Specifically, the three-dimensional printing method of a printed product having a cross-sectional pattern according to the present invention comprise a step of providing an ink of the receiving part of the ink extruding member, a step of preparing an ink extruded product having the same shape of the cross-sectional pattern as the printed product, by applying pressure into the ink retained in each partitioned space and extruding the ink through the extruding part, and a step of printing the ink extruded product on a plate. In the ink providing step, at least one ink may be provided as an ink printed product printed by a three-dimensional printing method, and at least one ink may be further provided as an ink filled product by a method other than the three-dimensional printing method.

The ink extruding member or the three-dimensional printing device comprising the ink extruding member, and the method for preparing a printed product with a cross-sectional pattern using the ink extruding member or the three-dimensional printing device comprising the ink extruding member will be described in detail by components of the device and steps of the method in the followings.

The ink extruding member according to the present invention comprises a ink-receiving part which comprises a partitioning member providing two or more spaces partitioned so as to have the same cross-sectional pattern as the printed product and receives each different ink for printing into spaces partitioned by the partitioning member, and an ink-extruding part which is positioned in the lower part of the ink-receiving part and is equipped with a single passage that inks pass and extrudes inks received in the ink-receiving part.

When using the ink extruding member according to the present invention, since the diameter of the ink-receiving part which is capable of printing and commercialized is very large, bio-inks are extruded and therefore the shear stress is hardly applied to inks or a cell contained therein. In addition, compared with the prior art using multiple heads containing multiple materials heterogeneously, the present invention can extrude two or more of different inks together using one ink extruding member to print, and thus a single printing head can be used and thereby the printing process time is reduced and the shear stress is hardly applied to inks or a cell contained therein. Therefore, when using inks containing a cell by using the printing method or device according to the present invention, there are advantages that the cell viability is high and the system becomes simple.

The extruding member is a component supplying an ink by pushing he ink by applying pressure from the outside, and it may be a cartridge or syringe commonly used for a three-dimensional printing device. For printing by extruding the ink, the pressure which is applied into the ink receiving member may be different depending on the concentration of the ink and the size of the nozzle, but it may be for example, 0.1 to 700 kPa, 1 to 500 kPa or 1 to 700 kPa. When the printing air pressure is high, too much material is extruded, and when the air pressure is low, the subsequent material can not be printed and slip inside the supporting material.

The ink extruding member is positioned in the lower part of the ink-receiving part and comprises a single passage making multiple inks pass and an ink-extruding part that extrudes the inks received in the ink-receiving part. The ink-extruding part equipped with a single passage can extrude the inks received in the ink-receiving part partitioned to a plurality of spaces, in the manner of single channel control instead of multiple channel control.

The inner diameter of the extruding port is very small. The inks received in the ink-receiving part can be extruded outside of the ink-receiving part through the extruding port. The extruded ink product discharged from the ink-extruding part has the same cross-sectional pattern as the cross-sectional pattern of the ink-receiving part, with the reduced size.

The three-dimensional printing device according to the present invention may further comprise a nozzle linked in the terminal of the ink-extruding part of the extruding member, and inks are discharged through the nozzle, and a plate is positioned in the lower part of the nozzle and the inks for printing discharged from the nozzle is deposited in the upper part of the plate, thereby preparing a printed ink product.

It is preferable that the printed ink product with a cross-sectional pattern according to the present invention is an artificial tissue of human body. For example, there are a muscular tissue (bundle structure), a bone tissue (lamellae & canal structure), a nervous tissue (perineurium structure), a blood vessel tissue (multi-layer structure), a spinal cord tissue, etc.

Even though it is necessary to reduce the diameter of a printing nozzle to increase the resolution of the bio-printing technique based on fused deposition modeling, since the smaller the diameter of the nozzle becomes, the more frequently the cell death are caused by the shear stress occurring between a material extruded from the inside of the nozzle and a wall surface of the nozzle. It is difficult to blindly downsize the diameter of the nozzle. Therefore, the high resolution can be achieved by applying an ink-receiving part which has the same cross-sectional pattern as the printed ink product and an ink-extruding part which extrudes the inks through a single passage.

The method for printing a biological tissue according to the present invention can control pressure so that the inks retained in the ink-receiving part have the same ratio as the pattern of the printed product but having an enlarged cross-sectional shape are provided into the ink-receiving part, and the cross-sectional pattern of the ink-receiving part maintains pass an ink-extruding part having a smaller cross-section than the cross-section of the ink-receiving part, with maintaining the pattern. It is preferable that the cross-sectional pattern of extruded ink product can be maintained to be the same cross-sectional pattern of the ink-receiving part.

According to the present invention, a microstructure which is complex structure and has a very small size, can be easily printed by using a big size of printing ink which can be comparatively easily prepared.

In the present specification, the meaning of "same" is defined not only to be identical at 100%, but also to include the same thing to the extent that the same function can be performed substantially. In the specification, "cross-section maintains the same shape" means that only the size of the cross-section becomes small, with maintaining the original shape of the cross-section as itself. Thereby, after making a printing material with a large cross-section which is easier to form in advance, it is possible to print a tissue cell corresponding to a desired size, namely the actual size.

It is preferable that the viscosity of the printing ink is in the level that the cross-section of the ink product extruded by passing a nozzle can maintain the same shape as the cross-section of the printing material.

The cross-section of the printed ink product is a small size that cannot be achieved according to the current bio-printing technology, or a microstructure having very low survival rate at the printing. As aforementioned, the printed product can be a muscular tissue (bundle structure), a bone tissue (lamellae & canal structure), a nervous tissue (perineurium structure), a blood vessel tissue (multi-layer structure), a spinal cord tissue, etc.

The cross-section of the ink-receiving part in the printing device according to the present invention may have the same cross-sectional pattern as the printed product, and the ratio of the cross-sectional pattern of the ink-receiving part and the cross-sectional pattern of the extruded ink product or the printed ink product may be represented by various methods such as an area ratio, and a diameter ratio of the cross-section and the like. The ratio(=B/A) of the cross-sectional pattern of the extruded product or the final printed product (B) to the cross-sectional pattern of the ink provided into the receiving part, for example the ratio of the diameter of the cross-section, or the ratio of the cross-sectional area may be downsized to a ratio of 100:99 to 100:0.1, 100:50 to 100:1, or 100:18 to 100:1. In addition, based on the cross-sectional diameter ratio or the cross-sectional area of the primary ink printed product provided by the three-dimensional printing method, the cross-sectional diameter ratio, or the cross-sectional area ratio of the secondary printed product of the primary ink printed product may be downsized to a ratio of 100:99 to 100:0.1, 100:50 to 100:1, or 100:18 to 100:1.

The ink in the ink-receiving part undergoes two steps of printing. When the downsizing ratio of the second printed ink product is represented with respect to the first printed product in the ink-receiving part, the downsizing ratio of the second printed ink product is shown as the difference of a diameter of the first printed product in the ink-receiving part and a diameter of the second printed product is divided by the diameter of the first printed product in the ink-receiving part, in the following formula 1.

$$\text{Downsizing ratio of printed ink product} = (A-B)/A \times 100(\%) \quad \text{[Formula 1]}$$

Wherein, A is a diameter of the first printed product in the ink-receiving part, B is a diameter of the second printed product, and A and B are represented by the same length unit.

The downsizing ratio of the second printed product is directly affected by the cross-sectional diameter of the ink-receiving part, the cross-sectional diameter of the ink-extruding part, or the diameter of the nozzle, etc., and it may be variously designed by properly adjusting it according to the cross-sectional pattern size of the printed ink product. The cross-sectional diameter of the printed ink product is changed according to the size of the nozzle, and the range of 0.1 mm to 1 mm may be commonly used, and it may be changed according to the printing process such as properties of ink materials, pressures, speed of a printing head, location of the printing product (printing bed), etc.

According to examples of the present invention, the ratio may be miniaturized from the total diameter (15 mm) of a certain shape (Example: Lobule) to 99% or 98.7% (200 μm).

In one embodiment of the present invention, the ratio of downsizing of the primary printing ink represented by the equation 1 (=(A−B)/A×100) may be 0.1% or more, 10% or more, 20% or more, 30% or more, 40% or more, 50% or more, 60% or more, 70% or more, 80% or more, 85% or more, 90% or more, 92% or more, 95% or more, or 99% or more, and for example, may be 0.1 to 99.9%, 50% to 99% or 45% to 99%.

Preferably, the ink provided into the ink extruding member according to the present invention is a bio-ink capable of preparing an artificial organ, etc. Specifically, the printing may be performed by providing different inks into each partitioned spaces of ink-receiving part equipped with a partitioning part providing two or more partitioned spaces so as to have the same shape of cross-sectional pattern as the printed product. The different inks mean the inks in which one or more selected from the group consisting of constituents, content of constituents and physical properties are different.

In the present specification, the "bio-ink" includes a living cell or bio-molecule, and is the materials capable of constructing a required structure by being applied to bio-printing technology. The bio-ink of the present invention includes a liquid, semisolid, or solid composition comprising a plurality of cells.

Therefore, the bio-ink can provide a physical property for a three-dimensional processing and a biological environment so that a cell performs a targeted function. It is preferable to properly supplying nutrients and oxygen required for the cell survival in the ink extruding member, when the printing process is performed in a long time. Moreover, a cell should be protected from a physical stress occurred in the printing process. In addition, the bio-ink should have physical properties required in the printing process that are repeatability and productivity of a three-dimensional patterning and no blockage of nozzle, etc.

It is preferable that the ink of the present invention is a hydrogel, and therefore may comprise a gelling polymer. For example, it may comprise one or more kinds selected from the group consisting of a gelling polymer, a cell, a growth factor and an extracellular matrix.

The bio-ink used in the present invention is for example, a hydrogel with or without including a desired cell. The hydrogel can be a hydrogel containing a growth factor, a hydrogel containing a cell and a growth factor, a hydrogel containing a cytokine, or different kinds of hydrogels each other, etc. It is proper that the hydrogel is collagen, matrigel, alginate, gelatin, agarose, cell ink derived from a cellularized tissue, hyaluronic acid, fibrin gel, etc. or a mixed hydrogel.

In addition, since the lower the viscosity, the faster the bio-ink spreads, a gel phase material having a viscosity measured at the temperature of 25° C. as a viscosity thicker than water (1 cp) of 2 cp to 1,000,000 cp, for example, a viscosity of 2 cp to 10,000 cp, 5 cP to 1,000,000 cP, 2 to 500 cp, 5 to 300 cp, etc. is suitable. When the viscosity of ink is too low, the shape of the ink printed product printed by the three-dimensional printing method may be collapsed or modified, and the ink printed product and the ink filled product may be mixed, thereby collapsing the boundary.

The viscosity of the gel form of material used for the method of the present invention is preferable to have an appropriate viscosity so that the printing material can be extruded in the extruding process described later. According to one embodiment of the present invention, it is preferable to provide a relatively high viscosity of ink compared to an inkjet method, since an extrusion-type three-dimensional printing method is applied. In one embodiment, an ink applicable to the present invention may use various viscosity enhancers, to provide an appropriate viscosity for extrusion. The viscosity of the printing material is such that the cross-section of the extruded product extruded by passing through a nozzle maintains the same shape as the cross-section of the printing material.

The difference of ink viscosities of the ink filled product and ink printed product, the difference of viscosities measured at 25° C. may be 5,000 cp or less, for example, 0 to 5,000 cp, 1,000 cp or less, 500 cp or less, 200 cp or less, 150 cp or less, 100 cp or less, 50 cp or less. When the viscosity difference of inks is very large, the shape of the ink printed product may be modified by molecular force of materials different each other, and in case of three-dimensional printing by extruding, when the same pressure is applied into the ink or ink receiving member, the ink pattern retained in the ink receiving member may be collapsed due to the viscosity difference. Therefore, when using two or more of inks different each other, it is preferable that the difference of viscosity is low.

The difference of elasticity value of the ink filled product and ink printed product may be 10,000 Pa or less, for example, 0 to 10,000 Pa. The ink filled product and the ink printed product are preferable that the viscosity and elasticity changes in accordance with the shear rate are similar and the viscosity value and the elasticity value are similar.

In addition, when gelling polymers used for the inks different each other are different, for example, when a gelling polymer is temperature-sensitive as a collagen, a gelatin, and the other is not temperature-sensitive as an alginate, a fibrin gel, there may be a need to control the temperature inside of the syringe. For example, the temperature of the ink receiving member may be suitably controlled in the temperature range of 4° C.~37° C.

A natural or synthetic hydrogel bio-ink has been developed and used in the three-dimensional bio-printing field currently, but the bio-ink based on a hydrogel is used as it is excellent in the physical and biological aspects such as biocompatibility, printing suitability, geometric precision, and precision.

The "extrusible" means capable of being molded by passing through an ink-extruding part, a nozzle or an orifice (e.g., one or more of holes or tubes) (for example, under pressure). In addition, the densification is induced from growing a cell to an appropriate density. The cell density required for the bio-ink differs from cells to be used and tissues or organs to be prepared.

In addition, the present invention provides a bio-ink composition, wherein the bio-ink composition further comprises a tissue-derived component. The tissue-derived component means a gelling material which a certain tissue of an animal such as cartilage, kidney, heart, liver, muscle, and the like is de-cellularized in and has extracellular matrix as a main component, and it may be comprised to intensify tissue specificity of the bio-ink composition.

In the present invention, the bio-ink composition may comprise a cell culturing medium additionally. The cell culturing medium is the concept including any medium suitable for a targeted cell.

The ink according to the present invention may comprise a gelling polymer, and various kinds of the gelling polymer solutions used for printing can be used, and conditions of the polymer solution should be as follows. First of all, to ensure that the three-dimensional printing can be performed well, spraying to a nozzle should be easy by having a proper viscosity, and a problem that the shape of the object produced by being rapidly cured after the discharge is disarranged and the like should not be occurred. In addition, fundamentally, for preparing purposes, it is necessary to create a cell culture environment similar to the tissue in the human body.

The example of the gelling polymer may be one or more selected from the group consisting of fucoidan, collagen, alginate, chitosan, hyaluronic acid, silk, polyimides, polyamix acid, polycarprolactone, polyetherimide, nylon, polyaramid, polyvinyl alcohol, polyvinylpyrrolidone, poly-benzyl-glutamate, polyphenyleneterephthalamide, polyaniline, polyacrylonitrile, polyethylene oxide, polystyrene, cellulose, polyacrylate, polymethylmethacrylate, polylactic acid (PLA), polyglycolic acid (PGA), copolymer of polylactic acid and polyglycolic acid (PLGA), poly{poly(ehtyleneoxide)terephthalate-co-butyleneterephrhalate} (PEOT/PBT), polyphosphoester (PPE), polyphosphazene (PPA), polyanhydride (PA), poly(ortho ester) (POE), poly(propylene fumarate)-diacrylate (PPF-DA) and poly(ethylene glycol) diacrylate (PEG-DA), or combinations of the materials. However, materials are not limited by the examples. In addition, the gelling polymer may be a chemically modified natural polymer, and for example, it may comprise GelMA in which gelatin and methacrylate (MA) are chemically combined and a photoinitiator is combined thereto, an alginate in which pentapeptide sequencing Tyr-Ile-Gly-Ser-Arg (YIGSR) and EDC/NHS are combined to add a binding site of alginate/gelatin, alginate, etc.

In particular, the hydrogel such as polyethylene glycol, alginate, collagen and gelatin has been widely used for preparation of a carrier in which a cell is embedded, since it has high water content and excellent biocompatibility and it can control mechanical properties and its biodegradability is excellent. Because of these reasons, the hydrogel is very suitable for preparation of a structure in which a cell is embedded, and it can directly print to obtain various types of tissue regeneration framework.

The gelatin exhibits a temperature-sensitive property, so it is specifically suitable for the cell delivery material. In other words, the gelatin is liquefied at 37° C. and it has a property to be solidified at the room temperature or below.

The gelling polymer can form a cross-link using a physical treatment or chemical treatment, and a cross-link solution may be used for the chemical treatment, and the cross-link solution may be selected and used properly according to the selected gelling polymer. For example, the cross-link solution may be a solution of a mixture of one or more kinds selected from the group consisting of plaster; or hydroxyapatite, carbonate apatite, fluorapatite, chlorapatite, α-TCP, β-TCP, calcium metaphosphate, tetracalcium phosphate, calcium hydrogen phosphate, calcium dihydrogen phosphate, calcium pyrophosphate, calcium carbonate, calcium sulfonate, EDC {1-ethyl-(3-3-dimethylaminopropyl) carbodiimide hydrochloride} or salts thereof.

The ink containing the gelling polymer is preferably formed so that the collagen concentration ratio in the liquid type of collagen solution is usually within a range of 0.1~30%. The method for preparation of hydrogel may be performed by applying common preparation methods used for preparing an ink for a three-dimensional printing, but not limited thereto.

The bio-ink according to the present invention may comprise a cell, and an applicable cell or tissue is not particularly limited, and it may be an animal cell or a plant cell, or a tissue of an animal or a plant. The cell may be one or more selected from the group consisting of stem cell, osteoblast, myoblast, tenocyte, neuroblast, fibroblast, glioblast, germ cell, hepatocyte, renal cell, Sertoli cell, chondrocyte, epithelial cell, cardiovascular cell, keratinocyte, smooth muscle cell, cardiomyocyte, glial cell, endothelial cell, hormone-secreting cell, immunocyte, pancreatic islet cell and neuron.

The cell type used in a prepared artificial tissue of the present invention may be cultured by any manner publicly known in the art. The method of culturing a cell and a tissue is publicly known in the art.

In addition, the cell may be cultured with a cell differentiation material which induces differentiation of cell according to a desired cell line. For example, a stem cell produces a certain range of cell type, by contacting a differentiation medium and being incubated. Multiple types of differentiation media are suitable. The stem cell may be incubated by contacting a differentiation medium including an osteogenic differentiation medium, a chondrogenic differentiation medium, an adipogenic differentiation medium, a neuronal differentiation medium, a cardiomyocyte differentiation medium, and an intestinal cell differentiation medium (e.g., intestinal epithelium).

Additionally, the cell may be cultured with a growth factor, cytokine, etc. The "growth factor" refers to a protein, polypeptide, or polypeptide complex comprising a cytokine, which is produced by the cell and can affect itself and/or various other adjacent or remote cells. Commonly, the growth factor affects the growth and/or differentiation of certain type of cells naturally or by reacting to multiple biochemical or environmental stimuli. Some, but not all, of the growth factors are hormones. Exemplary growth factors are insulin, insulin-like growth factor (IGF), nerve growth factor (NGF), vascular endothelial growth factor (VEGF), keratinocyte growth factor (KGF), fibroblast growth factor (FGF) comprising basic FGF (bFGF), platelet-derived growth factor (PDGF) comprising PDGFAA and PDGF-AB, bone morphogenetic protein (BMP) comprising BMP-2 and BMP-7, etc., transforming growth factor-beta (TGF-β) comprising TGFβ1 and TGFβ3, epidermal growth factor (EGF), granulocyte-macrophage colony-stimulating factor (GM-CSF), granulocyte colony-stimulating factor (G-CSF), interleukin-6 (IL-6), IL-8, etc.

The "bio-printing" in the present invention means using a three-dimensional accurate cell deposition (e.g., cell solution, cell-containing gel, cell suspension, cell concentrate, multi-cellular aggregate, multi-cellular body, etc.) through methodology commonly used with an automated, computer-assisted, three-dimensional prototyping device (e.g., bio-printer). 3D printing is performed by extruding a biodegradable polymer from a nozzle using a bio-plotter and laminating it on a stage.

Various kinds of tissue-like organs may be produced by the method. The pattern laminating a bio-ink composition or lamination arrangement may be determined by the size and diameter, etc. of the tissue-like organ to be prepared. In addition, the number of cells comprised in the bio-ink used for preparing the tissue-like organ may be adjusted according to kinds of cells, content of cell nutrients comprised in the bio-ink composition, etc. Moreover, the kind of cells comprised in the bio-ink composition may be variously changed according to the kind of the tissue-like organ to be prepared according to the method. Those skilled in the art will be able to select appropriate cells according to the kind of tissue-like organ to be prepared through the three-dimensional bio-printing and apply them thereto.

After the bio-ink composition is sprayed by the three-dimensional bio-printer and laminated, the cross-link of the bio-ink composition may be promoted, by heating it, or exposing it to ultraviolet rays, or adding a cross-link solution. This cross-link allows the laminated bio-ink composition to be completed in a harder structure. To promote the cross-link, a photo-initiator may be used.

In order to prepare an ink extruding member having the same cross-sectional pattern as the printed product or having the same or a different cross-sectional pattern in size, different inks are received in each of partitioned spaces of the ink extruding member ink-receiving part, and the pressure, for example, a piston is controlled so as to pass an extruding port which is equipped with a single passage that inks pass and extrudes inks. It is preferable to put the bio-ink into the ink-receiving part after putting a little amount of hydrogel to 0.1 mL to 2 mL in advance as a supporting material, so as not to pour out the bio-ink, after filling the bio-ink in the ink-receiving part. Then, a hydrogel may be added or not be added in a barrel. When printing again, at the beginning of printing, the filled hydrogel gets out, and then a desired shape is printed. When finishing the printing of the desired shape of the printed product, the hydrogel filled up comes out. The reason for adding a support material at the beginning and the latter is to ensure stable printing.

Hereinafter, with reference to accompanying drawings, the present invention will be described in detail.

FIG. 1, FIG. 2, FIG. 3, FIG. 4 and FIG. 5 are drawings schematically showing a process of providing an ink by a three-dimensional printing method into an ink receiving member according to one embodiment of the present invention.

In FIG. 1, the inside of the ink extruding member (10) is partitioned by plural spaces retaining each ink (11, 12, 13, 14). In FIG. 9, a bioprinting device applicable to an example of extruding 5 knds of inks (1, 2, 3, 4, 5) according to one example of the present invention is shown. The final object (50) is completed by pushing a cell liquid material retained in the ink extruding member (10) in direction A and extruding the printing ink through the extruding part (20) or nozzle (80). Then, a piston (60) is preferable to be controlled so that the cross-section of the printing material maintains the same shape and only the size is reduced, to pass a nozzle (20), and optionally a base may be a container in which a liquid material is contained.

When the pressure is too strong, there is a risk that the load applied to the nozzle is increased to cause damage or the hydrogel can not be smoothly discharged in the form of a thread and is discharged in an unbalanced shape in a lump, and when the pressure is too weak, smooth discharge from the nozzle may not be achieved. On the other hand, when the diameter is too small, risks when the pressure is strong may be occurred equally, as the discharge pressure becomes larger, and when the diameter is too big, the accuracy of a three-dimensional shape during preparation of a scaffold may be decreased. The afore-mentioned pressure range and diameter range are ranges so that the discharge of the hydrogel is appropriately smoothly and easily preceded and at the same time the accuracy of the scaffold shape to be prepared is achieved in the suitably desired level, considering all of the afore-mentioned points, and are experimentally determined.

For example, the printing method according to the present invention, may be proceeded by comprising a step of retaining an ink in the receiving part, a step of extruding the ink to the nozzle having an outlet diameter, for example, in the range of 0.1~1 mm, by applying pressure in the range of 0.1~700 kPa, 1 to 500 kPa or 1 to 700 kPa to the receiving part, and a step of printing the ink while the nozzle moves at a speed within the range of 1~700 mm/min by a moving part of the printing device. And then, the final object (50) is completed by pushing a cell liquid material retained in the ink extruding member (10) in direction A and extruding a printing material to the base (100) through the extruding part (20). Then, the piston is preferable to be controlled so that the cross-section of the printing material maintains the same shape and only the size is reduced, to pass the extruding part (20), and optionally the base may be a container in which a liquid material is contained.

In case of bio-printing by spraying a single material as in the prior art, as there is a limit on the size reduction of the nozzle inner diameter of the ink-extruding part, there is a limit on the volume reduction of the material. However, since the volume of inks extruded can be reduced in proportion to the number of multiple inks according to the present invention, precise spraying is possible compared with the prior art. Moreover, as the area of contact between each ink and the inner surface of the passage of ink-extruding part is reduced when the multiple inks pass through the passage of ink-extruding part (20), the shear stress generated is reduced as compared with when extruding a single material. Therefore, there is an advantageous effect on the cell activity compared with the prior art.

Advantageous Effects

According to the present invention, since the volume of extruded material can be reduced in proportion to the number of multiple inks, precise injection is possible compared with the prior art. In addition, when the multiple inks pass through a passage of the ink-extruding part or nozzle, the area of contact between respective materials and the inner surface of the nozzle passage is decreased, and the shear stress that occurs is also reduced as compared with when a single material is extruded. Therefore, there is an advantageous effect over the prior art in terms of improving cell activity and printing precision.

BRIEF DESCRIPTION OF DRAWINGS

FIG. 1 is a schematic drawing showing a process of preparing a filled product of the primary ink and a printed product of the secondary ink according to one example of the present invention.

FIG. 2 is a schematic drawing showing an ink extruding member in which a filled product of the primary ink and a printed product of the secondary ink in the spiral shape and an extruded product obtained therefrom according to one example of the present invention.

FIG. 3 is a schematic drawing showing an ink extruding member in which a filled product of the primary ink and a printed product prepared with three kinds of inks and an extruded product obtained therefrom according to one example of the present invention.

FIG. 4 is a drawing schematically showing one example of injecting inks into an ink extruding member by a three-dimensional printing method according to one example of the present invention.

FIG. 5 is a drawing schematically showing a method of injecting the secondary to septenary inks by a three-dimensional printing method, in addition to a filled product of the primary ink, into an ink extruding member according to one example of the present invention.

FIG. 6 is a photograph of a syringe and an extruding part equipped in the end of syringe showing the process of preparing a filled product of the primary ink and a printed product of the secondary ink according to Example 1.

FIG. 7 is a confocal microscopic photograph showing the result of printing using an extruded product obtained from an ink extruding member in which a filled product of the primary ink and a printed product of the secondary ink in the spiral shape are injected according to Example 1.

FIG. 8 is a confocal microscopic photograph showing the result of printing using a syringe in which a filled product of the primary ink and a printed product of the secondary ink are filled, and an extruded product obtained from the syringe, according to Example 2.

FIG. 9 is a drawing schematically showing an ink extruding member having a receiving part in which 5 different inks are filled according to one example of the present invention.

FIG. 10 is a drawing schematically showing an ink extruding member according to one example of the present invention.

MODE FOR INVENTION

The present invention will be described in more detail with reference to the following examples, but the scope of the present invention is not intended to be limited by the following examples.

Example 1: Syringe Comprising Ink Printed Product and Ink Filled Product

The primary hydrogel for filling of 3 w/v % sodium alginate was injected into a syringe which was an ink-receiving part of a three-dimensional printing device. To the syringe in which the primary hydrogel was injected, using a three-dimensional printing device equipped with a long nozzle, 3 w/v % sodium alginate containing green fluorescent particles was injected as the secondary hydrogel by a three-dimensional printing method. One example of specific preparation processes was conducted similarly to the method illustrated in FIG. 1. The ink shape printed on the syringe was photographed and shown in FIG. 2.

The primary hydrogel for filling and the three-dimensional printed hydrogel were printed on the syringe by the three-dimensional printing method using an extruded product obtained through an extruding part by applying pressure, and printed as 3 lines using 1.0 mm of nozzle size (nozzle I.D). When a nozzle, of which nozzle size (nozzle I.D) was 1 mm, was used, the length of the printed cross-section was 30 micrometers, and when a nozzle, of which nozzle size (nozzle I.D) was 2 mm, was used, the length of the printed cross-section was 70 micrometers.

As a result of fluorescent observation of the printed product with a confocal microscope, it was confirmed by the confocal microscope that the hydrogel containing green fluorescent particles was printed. The microscopic photograph was shown in FIG. 3. FIG. 6 shows the photograph of forming the primary hydrogel for supporting and the secondary hydrogel having a certain shape formed inside by the three-dimensional printing method, using an extruding member comprising an ink-receiving part, according to Example 1. FIG. 7 shows the result of observing the printed product with the confocal microscope, which was prepared by the three-dimensional printing method by extruding the ink-receiving part in which the primary hydrogel and the secondary hydrogel obtained according to Example 1 under pressure conditions. In other words, fluorescent observation of the extruded product with the confocal microscope was same as the drawing of FIG. 7. It showed that inks were printed as separated with high resolution according to the method of the present invention.

Example 2: Three-Dimensional Printing Using Various Sizes of Nozzles

Using the three-dimensional printing device using the same ink extruding member as Example 1, the printing of hydrogels with nozzle sizes of 18, 20, 22, 25 and 27 Gauge was confirmed with a confocal microscope. Specifically, internal diameters of each nozzle of 18, 20, 22, 25 and 27 Gauge were 0.82 mm, 0.63 mm, 0.41 mm, 0.28 mm and 0.1 mm. The confocal microscopic photograph was shown as FIG. 8.

FIG. 8 shows the result of confocal microscope observation showing the printing products of the primary hydrogel filled product and the secondary hydrogel printed product depending on the variation of nozzle size using an extruding member comprising an ink-receiving part according to Example 8. As shown in the cross-sectional view, it was possible to miniaturize in the same shape as the cross-sectional shape of the ink extruding member. According to examples of the present invention, the ratio could be miniaturized from the total diameter (15 mm) of a certain shape (Example: Lobule) to 98.7% (200 μm). It was calculated according to the equation.

$$\text{Downsizing ratio of ink printed product} = (A-B)/A \times 100(\%) \quad [\text{Equation 1}]$$

In the equation 1,

A is a diameter of the primary ink printed product provided in the syringe by the three-dimensional printing method, and B is a diameter of the secondary printed product of printing ink, and the A and B are units of the same length.

TABLE 1

| ink-receiving member (syringe) diameter | 9.3 mm | 9.3 mm | 9.3 mm | 9.3 mm | 9.3 mm |
|---|---|---|---|---|---|
| A | 1.38 mm | 1.38 mm | 1.38 mm | 1.38 mm | 1.38 mm |
| Nozzle diameter | 820 um | 630 um | 410 um | 280 um | 100 um |
| B | 190 um | 160 um | 90 um | 70 um | 30 um |
| Downsizing ratio(%) | 86.2 | 88.4 | 93.5 | 94.9 | 97.8 |
| Size reduction (=B/A × 100%) | 13.8 | 11.6 | 6.5 | 5.1 | 2.2 |

Example 3: Ink Printed Product Comprising 2 or More Inks

The primary hydrogel was injected into the same syringe as Example 1. To the syringe in which the hydrogel was injected, using a three-dimensional printing device equipped with a long nozzle, the ink printed products sequentially printing 3 w/v % sodium alginates containing green, blue and red fluorescent particles, respectively, were injected into the syringe, and the printing of the obtained RGB hydrogel was confirmed by a confocal microscope. The syringe filled with the ink printed products prepared with the three kinds of inks and the mimetic diagram of its preparation process were shown in FIG. 7.

According to the method of the present invention, it could be confirmed that not only an ink printed product could be prepared with one ink inside of a syringe, but also an ink printed product could be prepared with 2 or more inks by performing three-dimensional printing, and thus it could be confirmed that various shapes of tissues could be copied.

Example 4: Fabrication of Artificial Blood Vessel Having Lumen Structure 3 w/v % sodium alginate was injected into the same syringe as Example 1, and using a long nozzle, a temperature-sensitive hydrogel, 3% gelatin was injected into the inside of alginate using a printing method. When prepared complex hydrogels were printed on 200 Mm of calcium chloride, only the alginate gelation was induced and the gelatin was present without being gelled. When the printing structure was put in liquid of 37° C., the gelled alginate maintained the shape itself, but the gelatin was melted and formed the lumen structure.

Example 5: Fabrication of Blood Vessel Comprising Cell and Having Multiple Lumen Structures A blood vessel structure was copied, through a sequential method of injecting 3 w/v % sodium alginate into the syringe, injecting 3% alginate containing smooth muscle cells at a concentration of $1 \times 10^7$ cells/mL or more in the filled 3% alginate, using a three-dimensional printing device equipped with a long nozzle, and injecting 3% gelatin containing vascular endothelial cells at a concentration of $1 \times 10^7$ cells/mL or more in the alginate containing smooth muscle cells, by the same method as Example 4. Particularly, aortas or vena cavae of blood vessels were piled up in a quadruple cylinder structure, and through the method, not only a quadruple structure could be easily printed, but also controlling the size was possible. Moreover, a double structure of venules or a single structure of microvessels could be copied similarly.

DESCRIPTION OF SYMBOLS

10: ink extruding member
20: extruding part
40, 50: ink extruded product
80: ink extruding port (nozzle)
100: plate Although the present invention has been described with reference to the accompanying drawings, the scope of the present invention is determined by the following claims and is not intended to be limited to the aforementioned examples and/or drawings.

The invention claimed is:

1. A three-dimensional printing method comprising
a step of providing at least two inks, each of the at least two inks having an unique pattern is separately loaded into an ink-extruding member for three-dimensional printing comprising an ink receiving part and an ink extruding part equipped with a single passage which passes and extrudes the at least two inks,
a step of forming an extruded ink product discharged from the ink-extruding part by applying physical force to the ink-extruding member, and extruding the at least two inks ink through the single passage, and
a step of printing the extruded ink product on a plate, wherein each of the at least two inks is separately retained without being mixed prior to extrusion.

2. The method according to claim 1, wherein the printed ink product has a two-dimensional or three-dimensional pattern in the step of providing at least two inks.

3. The method according to claim 1, wherein a cross-section of the extruded ink product in the ink-extruding member and a cross-section of the extruded ink product have the same pattern.

4. The method according to claim 1, wherein one of the at least two inks has 2 cp to 1,000,000 cp of viscosity measured at 25° C.

5. The method according to claim 1, wherein the viscosity difference between the filled ink product and the printed ink product is 0 to 5,000 cp.

6. The method according to claim 1, wherein the elasticity difference between the filled ink product and the printed ink product is 0 to 10,000 Pa.

7. The method according to claim 1, in the step of providing at least two inks, and the printed ink product are provided into the ink-extruding member simultaneously or sequentially.

8. The method according to claim 7, in the step of providing at least two inks, the ink printed product formed by a three-dimensional printing method is provided after providing the filled ink product.

9. The method according to claim 1, wherein the ink-extruding member comprises an ink receiving part which retains the ink in the internal space and an ink extruding part positioned in the lower part of the ink receiving part and equipped with a single passage which the ink retained in the receiving part passes and is extruded through.

10. The method according to claim 1, wherein a ratio of a cross-sectional diameter of the ink provided in the ink-extruding member and a cross-sectional diameter of the extruded ink product is 100:99 to 100:0.1.

11. The method according to claim 1, wherein the printed product is an artificial tissue.

12. The method according to claim 1, wherein the step of preparing the extruded ink product is performed simultaneously or sequentially with the step of providing ink.

13. The method according to claim 1, wherein the ink has different one or more kinds selected from the group consisting of components, content of ink components and physical properties of ink components.

14. The method according to claim 1, wherein the ink comprises a gelling polymer.

15. The method according to claim 1, wherein the at least two inks comprise one or more kinds selected from the group consisting of a gelling polymer, a cell, a growth factor and an extracellular matrix.

16. The method according to claim 1, wherein the ink-extruding member is equipped with a single passage which passes and extrudes the ink retained in the receiving part.

17. The method according to claim 1, wherein the step of applying physical force to the ink-extruding member is performed for extruding the ink to an extruding part, to prepare an extruded ink product having the same cross-sectional pattern as the printed product.

18. The method according to claim 1, wherein the extruded ink product released from the ink-extruding part has the same cross-sectional pattern as the cross-sectional pattern of the ink-receiving part, with the reduced size.

* * * * *